US005466659A

United States Patent [19]

Keeney et al.

[11] Patent Number: 5,466,659
[45] Date of Patent: Nov. 14, 1995

[54] TRICLOPYR BUTOXYETHYL ESTER COMPOSITIONS COMPRISING VEGETABLE OIL ESTERS AS CARRIERS

[75] Inventors: F. Nelson Keeney; John L. Troth, both of Carmel, Ind.

[73] Assignee: DowElanco, Indianapolis, Ind.

[21] Appl. No.: 240,797

[22] Filed: May 10, 1994

Related U.S. Application Data

[63] Continuation of Ser. No. 6,101, Jan. 15, 1993, abandoned.

[51] Int. Cl.$^6$ .......................... A01N 25/02; A01N 43/40
[52] U.S. Cl. ..................... 504/130; 504/254; 71/DIG. 1
[58] Field of Search .................................. 504/130, 254; 71/DIG. 1

[56] References Cited

U.S. PATENT DOCUMENTS

| | | | |
|---|---|---|---|
| 3,756,801 | 9/1973 | Herschler | 71/65 |
| 4,822,407 | 4/1989 | Esposito | 504/130 |
| 4,999,048 | 3/1991 | Freepons | 71/DIG. 1 |
| 5,037,654 | 8/1991 | Puritch et al. | 424/405 |

FOREIGN PATENT DOCUMENTS

| | | |
|---|---|---|
| 8322827 | 7/1984 | Australia . |
| 737861 | 7/1966 | Canada . |
| 1167271 | 5/1984 | Canada . |

OTHER PUBLICATIONS

Schneider, W. G., Efficacy, Uptake, and Translocation of Stem Applied Triclopyr Ester in Four Formulation Solvents, Dec. 1991.
Schneider, W. G. et al, Uptake and Translocation of Triclopyr in Spalings Following Basal Application, Abstract from Southern Weed society Proceedings 45th Annual Meeting, Jan. 20, 21, 22, 1992.
Rhodenbaugh, E. J. et al, Aromatic 200, Mineral Oil and Vegetable Oil as Triclopyr Carriers for Basal Bark Control of Hardwood Competition, Abstract from Southern Weed Society Proceedings 45th Annual Meeting, Jan. 20, 21, 22, 1992.
Schneider, W. G. "Efficacy, Update, and Translocation of .. . Triclopyn . . . " Thesis. Dec. 1991.
*The Agrochemicals Handbook* "Triclopyr", Picloram 1987.

*Primary Examiner*—S. Mark Clardy

[57] ABSTRACT

This invention relates to novel triclopyr butoxyethyl ester (triclopyr BEE) compositions comprising the use of esters of vegetable oils as carriers in triclopyr BEE compositions for use in the control of undesirable vegetation. The present invention further relates to a method for controlling undesired vegetation in which the novel triclopyr BEE composition is applied to the bark or stem of the vegetation.

34 Claims, No Drawings

TRICLOPYR BUTOXYETHYL ESTER COMPOSITIONS COMPRISING VEGETABLE OIL ESTERS AS CARRIERS

This is a continuation of application Ser. No. 08/006,101 filed Jan. 15, 1993, now abandoned.

FIELD OF THE INVENTION

This invention relates to novel triclopyr butoxyethyl ester (triclopyr BEE) compositions comprising the use of esters of vegetable oils as carriers in triclopyr BEE compositions for use in the control of undesirable vegetation. These ester carriers are especially useful in basal or stem application of triclopyr BEE compositions to control brush and woody vegetation. The present invention further relates to a method for controlling undesired vegetation in which this novel triclopyr BEE composition is applied to the bark or stem of the vegetation desired to be controlled.

BACKGROUND

Today's increased attention to nature and the environment has resulted in unprecedented efforts to encourage grasses, low-growing ground cover, and wildflowers on rights-of-way. Thus, individual plant control treatments are desirable to remove tall-growing woody plants low-profile vegetation control programs. Not only do such treatment programs result in effective, long lasting brush control, they leave non-target plants virtually untouched. This allows annual and perennial grasses and other desired plants to thrive because they are freed from competition for moisture, nutrients and sunlight.

One such treatment program consists of the use of basal bark or stem application of a herbicide to control undesired vegetation. As previously stated, control of such undesired vegetation is typically desirable along roadway, drainage and utility right-of-ways. This particular method is attractive because it provides not only vegetation control, but also efficient placement and utilization of the herbicidal composition on an individual basal bark or stem placement. Unlike nonselective herbicidal products or methods which can damage desirable grasses or plants, the present invention promotes the development of desired ground cover resulting in aesthetically pleasing rights-of-way.

Basal bark or stem applications of herbicidal compositions requires the herbicide to pass through the bark into the appoplast or symplast of the plant where movement to the site of activity can take place. It is well known that when applying the herbicide by basal or stem application, it is desirable to dissolve the herbicide in a non-aqueous organic carrier. As currently used, such carriers consist of petroleum distillates, such as fuel oils, for example, diesel oil or kerosene. These petroleum distillate carriers provide for penetration of the herbicide through the bark of the vegetation to be controlled.

However, these carriers present risks not only to the surrounding environment, but also to the applicator as well. When making basal or stem applications, application technique and packaging may not eliminate all contact of the herbicidal composition with skin or clothing. Also, due to applicator technique or wind conditions, over-spray onto surrounding areas may result during the application. Herbicide carriers such as diesel fuel and kerosene, are low grade petroleum products containing impurities, such as benzene, benzene(a)pyrene, and polycyclic aromatic hydrocarbons, and may pose a potential risk to human health. Thus, in order to pose less environmental and applicator exposures to petroleum distillates, new alternative herbicidal carriers are desirable in efforts to control undesired vegetation. In addition, new carriers which may increase uptake, translocation, or efficacy of the active herbicide are also desirable.

SUMMARY AND DESCRIPTION OF THE INVENTION

This invention provides novel triclopyr BEE compositions comprising the use of esters of vegetable oils as carriers in the compositions for use in basal or stem application of the herbicidal composition. These esters are potentially less hazardous to the environment or applicator. They also surprisingly increase the uptake and translocation of the herbicide to its site of action in the vegetation desired to be controlled, and further may provide desirable physical characteristics, such as, for example, low volatility, high flash point, low odor, stable shelf life, and a broad operating temperature range.

Suitable esters of vegetable oils employed in the present invention may include esters of corn oil, soybean oil, sunflower oil, canola oil, and cotton seed oil. Preferred are those of soybean oil, sunflower oil, and canola oil. Further preferred esters of vegetable oils include $C_1$–$C_4$ straight and branched chain alkyl esters of fatty acids, both saturated and unsaturated, ranging from $C_6$ to $C_{18}$. Saturated fatty acid esters include, for example, caproate, caprylate, caprate, laurate, myristate, palmitate, margarate, and stearate. Unsaturated fatty acid esters include, for example, myristoleate, palmitoleate, oleate, linoleate, and linolenate. Methyl fatty acid esters are preferred, and further, the unsaturated fatty acid esters are preferred over the saturated fatty acid esters. Preferred fatty acid esters employed in the present invention include methyl caprylate-caprate (Emery 2209, Henkel Corporation), methyl laurate (Emery 2296, Emery 2290, or Emery 2270, Henkel Corporation), and methyl oleate (Emery 2301, Henkel Corporation). A more preferred fatty acid ester is methyl oleate.

Triclopyr BEE is the common name for 3,5,6-trichloro-2-pyridynloxyacetic acid, butoxyethyl ester. This compound is a selective systemic herbicide used in the control of brush and woody vegetation, and many broad-leaved weeds, in areas such as grasslands and other uncultivated lands, industrial areas, rights-of-way, coniferous forests, oil palm and rubber plantations. It is available as a ready-to-use liquid formulation composition (Pathfinder™, DowElanco). It is also available as a ready-to-use liquid formulation composition in combination with picloram EHE (the common name for 4-amino-3,5,6-trichloropyridine-2-carboxylic acid, 2-ethylhexyl ester), a selective systemic herbicide used in the control of many annual and perennial broad-leaved weeds on grasslands and non-crop areas (Access™, DowElanco).

These novel triclopyr BEE compositions may be prepared by adding the desired amount of technical grade triclopyr BEE to the desired amount of one or more esters of vegetable oil carriers with agitation. The amount of the triclopyr BEE (by % weight) in the final composition may be generally from about 4% to about 75%, or the extent of solubility. Concentrations from about 4% to about 40% by weight are often preferred. Concentrations from about 4% to about 20% by weight are often more preferred.

The amount of triclopyr BEE present in the final treating composition is usually sufficient to provide control of undesired vegetation at a rate of from about 1 ml/inch stem diameter of the triclopyr BEE composition to about 5 ml/inch stem diameter of the triclopyr BEE composition, or preferably, about 3 ml/inch stem diameter of the triclopyr BEE composition. The actual dose will depend, of course, on the concentration of triclopyr BEE in the final composition.

The amount of ester of the vegetable oil carrier in the final composition will thus correspondingly range generally from about 60% to about 96% by weight, or preferably, from about 80% to about 96% by weight.

The present invention further provides a new method for treating undesired vegetation comprising applying the novel triclopyr BEE compositions to the vegetation desired to be treated. More specifically, this invention provides a method for controlling brush and woody vegetation which comprises the basal or stem application of a herbicidally effective amount of a fatty acid ester triclopyr BEE composition to the vegetation desired to be treated.

In addition to the compositions and uses set forth above, the present invention also embraces the composition and use of these triclopyr BEE compositions in combination with one or more additional compatible ingredients. Other additional ingredients may include, for example, one or more other herbicides, dyes, and emulsifiers, and any other additional ingredients providing functional utility, such as, for example, stabilizers, fragrants, viscosity-lowering additaments, and freeze-point depressants.

Additional herbicidal compounds are employed as supplements or additaments and should not be antagonistic to the activity of the triclopyr BEE composition as employed in the present invention, and can include, for example, the compound picloram EHE. Additional herbicidal compounds can be generally present in any herbicidally effective ratio in combination with triclopyr BEE, for example, picloram EHE is generally used in a ratio of about 1:2 to 1:6 picloram EHE:triclopyr BEE.

Dyes may be used in the formulated composition as a marker. Generally, a preferred dye can be any oil-soluble dye selected from EPA's list of approved list of inerts exempt from tolerance. See generally, 40 C.F.R. § 180.1001, parts c, d, and e. Such dyes, may include, for example, D&C Red #17, D&C Violet #2, and D&C Green #6. Dyes are generally added to the composition by adding the desired amount of dye to the formulated composition with agitation. Dyes are generally present in the final formulation composition in a concentration of about 0.1–1.0% by weight.

Emulsifiers may be used in the formulated composition as an aid in being able to rinse with water the container holding the formulated composition. Generally, any oil-soluble emulsifier, which on dilution with water forms an oil-in-water emulsion, can be selected for inclusion in the final formulated composition. A preferred emulsifier is Emgard 2033 (a nonionic emulsifier blend, Henkel Corporation). Emulsifiers are generally added to the composition by adding the desired amount of emulsifier to the formulated composition with agitation. Emulsifiers are generally present in the final formulation composition in a concentration of about 0.5–2.0% by weight.

The following nonlimiting examples further illustrate the present invention. All percentages given are by weight unless otherwise specified.

EXAMPLE 1

A herbicidal composition according to the formula (by % weight):

| | |
|---|---|
| triclopyr BEE | 4.5% |
| methyl oleate | 95.5%* |
| (Emery 2301, Henkel Corporation) | |

(*contains inerts associated with the technical triclopyr BEE)

was prepared by adding 47 g of the technical grade triclopyr BEE to 953 g of the methyl oleate with agitation to produce a composition with concentration of triclopyr BEE of 0.25 lb a.e.(acid equivalent)/gal.

EXAMPLE 2

A herbicidal composition according to the formula (by % weight):

| | |
|---|---|
| triclopyr BEE | 13.6% |
| methyl oleate | 86.4%* |
| (Emery 2301, Henkel Corporation) | |

(*contains inerts associated with the technical triclopyr BEE)

was prepared by adding 142 g of the technical grade triclopyr BEE to 858 g of the methyl oleate with agitation to produce a composition with concentration of triclopyr BEE of 0.75 lb a.e./gal.

EXAMPLE 3

A herbicidal composition according to the formula (by % weight):

| | |
|---|---|
| triclopyr BEE | 18.1% |
| methyl oleate | 81.9%* |
| (Emery 2301, Henkel Corporation) | |

(*contains inerts associated with the technical triclopyr BEE)

was prepared by adding 189 g of the technical grade triclopyr BEE to 811 g of the methyl oleate with agitation to produce a composition with concentration of triclopyr BEE of 1.0 lb a.e./gal.

EXAMPLE 4

A herbicidal composition according to the formula (by % weight):

| | |
|---|---|
| triclopyr BEE | 11.7% |
| picloram EHE | 1.9% |
| methyl oleate | 86.4%* |
| (Emery 2301, Henkel Corporation) | |

(*contains inerts associated with the technical triclopyr BEE and technical picloram EHE)

may be prepared by adding 122 g of the technical grade triclopyr BEE and 22 g of the technical grade picloram EHE to 856 g of the methyl oleate with agitation to produce a composition with concentration of triclopyr BEE of 0.74 lb a.e/gal. and concentratration of picloram EHE of 0.11 lb a.e./gal.

EXAMPLE 5

A herbicidal composition according to the formula (by % weight):

| triclopyr BEE | 13.6% |
| D&C Red #17 | 0.1% |
| methyl oleate | 86.3%* |
| (Emery 2301, Henkel Corporation) | |

(*contains inerts associated with the technical triclopyr BEE)

may be prepared by adding 142 g of the technical grade triclopyr BEE and 1 g of the dye to 857 g of the methyl oleate with agitation to produce a composition with concentration of triclopyr BEE of 0.75 lb a.e./gal.

EXAMPLE 6

A herbicidal composition according to the formula (by % weight):

| triclopyr BEE | 13.6% |
| emulsifier | 1.0% |
| (Emgard 2033, Henkel Corporation) | |
| methyl oleate | 85.4%* |
| (Emery 2301, Henkel Corporation) | |

(*contains inerts associated with the technical triclopyr BEE)

may be prepared by adding 142 g of the technical grade triclopyr BEE and 10 g of the emulsifier to 848 g of the methyl oleate with agitation to produce a composition with concentration of triclopyr BEE of 0.75 lb a.e./gal.

EXAMPLE 7

A herbicidal composition according to the formula (by % weight):

| triclopyr BEE | 13.6% |
| methyl caprylate-caprate | 43.2% |
| (Emery 2209, Henkel Corporation) | |
| methyl oleate | 43.2%* |
| (Emery 2301, Henkel Corporation) | |

(*contains inerts associated with the technical triclopyr BEE)

may be prepared by adding 142 g of the technical grade triclopyr BEE to 429 g of the methyl caprylate-caprate and 429 g of the methyl oleate with agitation to produce a composition with concentration of triclopyr BEE of 0.75 lb a.e./gal.

EXAMPLE 8

These studies evaluated the efficacy and uptake and translocation of triclopyr BEE in four different carriers, aliphatic (Exxsol D-80, $C_{11}/C_{12}$ dearomatized aliphatic petroleum hydrocarbons, Exxon Corporation), aromatic (Aromatic 200, $C_{11}/C_{12}$ petroleum alkylbenzenes, Exxon Corporation), kerosene (kerosene 1-K, mixture of petroleum hydrocarbons), and methylated fatty acid ester (MFAE) (Emery 2301, methyl oleate, Henkel Corporation), following stem application to three different species, red maple (*Acer rubrum*), white oak (*Ouercus alba*), and Virginia pine (*Pinus virginiana*).

Methods and Procedures (Efficacy field study): This study was performed at two powerline rights-of way sites in the state of Virginia, U.S.A. Both sites were bordered by forests which are predominately oak. Vegetation species included Virginia pine, red maple, red oak, rhododendron, white oak, chestnut oak, table-mountain pine, black birch, greenbriar, and blackberry.

Thirty-six triclopyr BEE treatments consisting of a factorial arrangement of twelve formulation compositions (four carriers containing three triclopyr BEE concentrations) and three doses were each randomly assigned to 25 stems of each of three species, red maple, white oak, and Virginia pine. Concentrations were 0.25, 0.5 and 1.0 lb a.e. of triclopyr BEE per gallon. Doses were 1, 3, and 5 ml of formulation composition per 2.5 cm of stem diameter measured at 15 cm above the groundline. Trees less than 0.5 cm in stem diameter and those in sprout clumps were avoided if possible.

Prior to application, 900 stems of each species were tagged; measured for diameter at 15 cm above groundline, height, and crown width; and randomly assigned a treatment. After measuring stem diameter, the precise dose for that tree was calculated and written on the tag. The trees were also flagged by color according to the concentration of triclopyr BEE they would receive.

Triclopyr BEE applications were made during the month of June. Solutions were contained in one liter plastic bottles which were carried in buckets. Tygon tubing was inserted through the lid of the bottles onto which a syringe was connected and solution withdrawn. Applicators were alternated each day between the three concentrations to avoid confounding concentrations with applicator. Application was made within the lower two feet of each stem using a 10 ml syringe. No attempt was made to wet the whole two feet of stem; however, an attempt was made to at least encircle each stem with a band of solution. Better coverage of stem surface occured among maples and small oaks. The solutions tended to soak into the pines and larger oaks and not visibly spread as much. Live crown widths, in two perpendicular axes, and heights of each tree were remeasured in the next month of August.

Trees which showed no signs of herbicidal damage after 14 months were assumed not to have received treatment and not included in the analysis if virtually all other trees receiving the same treatment were dead. After removing the above trees and those not found during remeasurement, 2501 out of 2700 remained, plus 64 control trees. Each treatment was represented by at least 19 of the original 25 replicates.

Methods and Procedures (Uptake and Translocation laboratory study): This study was performed on trees removed from a forest site in the state of Virginia, U.S.A. During the winter season, 150 saplings each of red maple, white oak, and Virginia pine were removed from the forest understory. Enough soil was retained with the roots to fill a fifteen liter pot and the roots were clipped to the same size. The branches of the trees were also pruned back due to the smaller root system now available to support them. The saplings were placed in a greenhouse and allowed to grow and become acclimated to the pots until the following July. At this time, approximately 100 of each species were alive. The saplings were then sorted and 40 of those with the largest and healthiest-looking crowns were selected for treatment.

Unformulated $C^{14}$-labeled triclopyr BEE (specific activity=30.5 µCi/µmole) was mixed with unlabeled triclopyr BEE formulated at 1 lb a.e. per gallon in each of the four carriers. The amount of labeled triclopyr BEE was so small, compared to the unlabeled triclopyr BEE, that it had negligible effect on concentration. The resulting solutions contained activities of approximately 1 µCi per ml.

To minimize solution dripping down stems, a dose of 150 µl per 1 cm of stem diameter measured at 15 cm above groundline, using 1 lb a.e. per gallon, was used. When this dose was not enough to encircle stems, often only one side was treated. At treatment time, a roll of plastic-backed absorbent paper was placed on the ground. Thin marks encircling the stems were made at 15 and 30 cm above the groundline using a grease pencil. These marks delineated the treatment zone and had the added benefit of helping to contain the solution on smooth-barked stems as did laying the saplings down and treating the stems horizontally. After the solutions had adequately penetrated, or the carrier had evaporated so that dripping was no longer a problem, the saplings were returned to a greenhouse. All saplings were watered at the end of the day and periodically thereafter. These treatments were repeated the following February and May on the remaining trees.

Harvests occured three weeks after each treatment. Harvest involved cutting the stem into segments, including the treated stem section, the roots, the leaves, and stem segments above and below the treatment area. All the sections were placed in a common paper bag except the treated stem section which was placed in a separate bag. The soil was washed from the roots, and they were set out to dry, and later bagged. All material but the treated stem sections was placed in an oven at 60° C. to dry for two weeks. The treated sections were kept frozen in an attempt to reduce further herbicide penetration and reduce evaporation of herbicide from the bark surface. Later, the treated stem sections were divided into three fractions, the outer bark, the inner bark, and the wood, and each fraction was ground. All leaves were removed from each sapling and mixed together. Subsamples from the leaves of each sapling were ground. Samples of root bark were also removed and ground. In general, grinding was more complete on larger samples and on non-fibrous material.

Two subsamples were taken from each ground fraction, except where two portions were ground, i.e., in the case of the leaves. Also, because so little activity was found in the first root bark subsamples, a second was only analyzed when activity was found in the first to determine if the result was reproducible. Each subsample was weighed to the nearest mg and then combusted in an OX-500 biological material oxidizer (R. J. Harvey Instruments Corp., Hillsdale, N.J.). The combustion gases, which contained the $C^{14}$ as $^{14}CO_2$, were bubbled through $C^{14}$ solution (R. J. Harvey Instruments Corp. Hillsdale, N.J.), absorbing the $^{14}CO_2$ in solution. This solution was then assayed in a Beckman LS-250 liquid scintillation counter (Beckman Instruments, Inc., Columbia, Md.). After subtracting a background level of 60 cpm's as determined from leaf material, subsample cpm's were divided by the counter efficiency to convert to dpm's and then multiplied by the oxidizer correction factor and by the ratio of the weight of the whole section to the weight of the subsample to get activity present in a given section. The percent of applied activity found in a section was then assumed to be proportional to the amount of unlabeled herbicide present. The two subsample values were then averaged for the analysis. One untreated tree from each species was also harvested from each treatment month.

The response variable was percent of applied $C^{14}$ found in each section of the sapling. Analysis of variance was performed by section, i.e., leaves; outer bark, inner bark, and wood from the treated section; and roots, on arcsin transformed data.

Because carrier evaporation was noted following treatment, a test of triclopyr BEE evaporation was carried out. The same solutions applied to the saplings were used in this test. A 10 μl drop of each solution was placed on each of three glass slides and three slices of maple bark, approximately 1 cm×2 cm, each resting on a glass slide. A 10 μl drop was also placed directly into each of three glass scintillation vials as a standard and 10 ml of Ecoscint scintillation solution (National Diagnostics, Manville, N.J.) added. They remained there from 11:30 AM to 5:30 PM on a warm, sunny day. After this period, the slides were washed with the same carrier in which the triclopyr BEE had been diluted. A 1 ml wash was followed by a 0.5 ml wash, and then the slide was wiped with a tissue. Each wash and the tissue were placed in a scintillation vial to which 18 ml of Ecoscint was added. The slice of bark was placed in a scintillation vial and later oxidized as described above for tissue samples.

Relative rates of carrier evaporation were also determined. Similar amounts of each formulation carrier, weighing approximately four grams, were placed into three petri dishes with a surface area of 60 cm³. Weights were remeasured after 1, 3, 7, and 24 hours. The experiment was performed in a fume hood at 26° C.

Results (Efficacy field study): The analysis showed species, formulation, and dose to be significant factors in the model ($p<0.0001$). In addition, all interactions between formulation, species, and dose were significant ($p=0.0007$ or less).

Overall, the aliphatic, MFAE, and kerosene formulations gave very similar crown volume control and mortality, whereas the aromatic treatments produced about three-quarters the control and half the mortality.

Results (Uptake and Translocation laboratory study): The analysis showed significant species and carrier main effects ($p<0.007$).

Recovery of applied $C^{14}$-labeled triclopyr BEE was less in the outer bark and, correspondingly, more inside the saplings with the MFAE formulation than with the other three formulations. Among the other carriers, about the same distribution of activity among outer bark and other tree fractions was found. In particular, activities in the inner bark, wood, and leaf fractions were greater with MFAE than with other carriers. Therefore, penetration or uptake of herbicide was greater when formulated in the MFAE carrier than with the other carriers.

Further results from the Efficacy study and Uptake and Translocations study are shown in the following tables:

TABLE 1

Average dimensions of trees used in the Efficacy study and the Uptake and Translocation study[1]:

| STUDY | DIMENSION | SPECIES | | |
|---|---|---|---|---|
| | | MAPLE | OAK | PINE |
| EFFICACY | DIAMETER (cm) | | | |
| | -average | 2.13 c | 3.57 b | 5.15 a |
| | -range | 0.5–11.0 | 1.0–10.0 | 1.5–13.0 |
| | HEIGHT (m) | | | |
| | -average | 2.02 c | 3.16 a | 2.90 b |
| | -range | 0.6–6.0 | 0.7–9.0 | 0.2–6.1 |
| UPTAKE | DIAMETER (cm) | | | |
| | -average | 2.02 b | 2.80 a | 2.94 a |
| | -range | 1.3–3.2 | 1.5–4.6 | 2.1–4.3 |
| | BARK THICKNESS | | | |

TABLE 1-continued

Average dimensions of trees used in the Efficacy study and the Uptake and Translocation study[1]:

| STUDY | DIMENSION | SPECIES | | |
|---|---|---|---|---|
| | | MAPLE | OAK | PINE |
| | (mm) | | | |
| | -average | 0.83 c | 2.06 a | 1.27 b |
| | -range | 0.5–1.5 | 1.0–3.5 | 0.5–2.6 |

[1]Values within a row followed by the same letter are not significantly different (Duncan's NMRT, alpha = 0.05).

TABLE 2

Mean percent crown volume control and percent mortality across species, concentrations, and doses amoung trees treated with triclopyr BEE formulated in four carriers:

| CARRIER | CROWN VOLUME CONTROL[1] | MORTALITY ($p < 0.001$)[2] |
|---|---|---|
| AROMATIC | 75 b | 51 |
| ALIPHATIC | 100 a | 94 |
| MFAE | 100 a | 95 |
| KEROSENE | 100 a | 93 |

[1]Values followed by the same letter are not significantly different (Duncan's NMRT, alpha = 0.05).
[2]P-value, determined by chi-square test, for the independence of mortality and carriers.

TABLE 3

Mean percent of applied activity across species and treatment months recovered in saplings three weeks after stem application of triclopyr BEE[1] formulated in four carriers:

| TREE SECTION | FORMULATION SOLVENT | | | |
|---|---|---|---|---|
| | AROMATIC | ALIPHATIC | MFAE | KEROSENE |
| Outer bark[3] | 78.62 a[2] | 78.01 a | 69.91 b | 77.71 a |
| Inner bark[4] | 1.23 b | 1.23 b | 2.91 a | 1.21 b |
| Wood[5] | 0.42 b | 0.67 b | 2.12 a | 0.50 b |
| Leaves[6] | 0.21 c | 0.48 b | 1.82 a | 0.44 b |
| Roots[7] | 0.001 a | 0.005a | 0.013a | 0.002a |
| Total | 81.94 a | 82.21 a | 81.05 a | 81.05 a |
| Uptake[8] | 2.41 b | 3.14 b | 8.96 a | 2.85 b |

[1]Solution was applied at a dose of 150 µl/cm of stem diameter and contained primarily unlabeled triclopyr BEE (1 lb a.e./gal) along with 0.8–0.9 µCi of $C^{14}$-triclopyr/ml.
[2]Values within a row followed by the same letter are not significantly different (Duncan's NMRT, alpha = 0.05).
[3]Outer bark of treated stem section.
[4]Inner bark of treated stem section.
[5]Wood of treated stem section.
[6]Total leaves.
[7]Band of root bark 2–3 cm wide removed from 3–10 cm below groundline.
[8]Uptake = Inner bark + Wood + Leaves + Roots.

TABLE 4

Mean percent of applied activity across treatment months recovered inside[1] red maple, white oak, and Virginia pine saplings three weeks after stem application of triclopyr BEE[2]:

| | FORMULATION SOLVENT | | | |
|---|---|---|---|---|
| SPECIES | AROMATIC | ALIPHATIC | MFAE | KEROSENE |
| MAPLE | 5.32 bA[3] | 6.47 bA | 26.31 aA | 6.29 bA |
| OAK | 1.20 bB | 1.79 abB | 2.89 aB | 1.77 abB |
| PINE | 1.55 bB | 2.03 bB | 3.78 aB | 1.75 bB |

[1]Includes recoveries from Inner bark, Wood, Leaves, and Root bark.
[2]Solution was applied at a dose of 150 µl/cm of stem diameter and contained primarily unlabeled triclopyr BEE (1 lb a.e./gal) along with 0.8–0.9 µCi of $C^{14}$-triclopyr/ml.
[3]Values within a row followed by the same lowercase letter and values within a column followed by the same uppercase letter are not significantly different (Duncan's NMRT, alpha = 0.05).

TABLE 5

Amount of $C^{14}$-labeled triclopyr BEE formulated in four solvents remaining on a slide or a piece of bark after six hours as determined by washing the slides and oxidizing the bark[1]:

| | $C^{14}$ACTIVITY (dpm - 1 standard deviation) | | |
|---|---|---|---|
| SOLVENT | STANDARD[2] | SLIDE | BARK |
| ALIPHATIC | 19,801–380 | 19,311–291 | 20,422–682 |
| AROMATIC | 18,967–236 | 19,437–782 | 20,958–2040 |
| KEROSENE | 20,187–165 | 18,625–744 | 21,305–174 |
| MFAE | 20,555–3157 | 20,092–3258 | 23,696–3163 |

[1]Three replicate 10 µl drops of solution containing both $C^{14}$-labeled and unlabeled triclopyr were placed on slides or bark surfaces.
[2]Drops were placed directly into scintillation vials to which scintillation fluid was immediately added.

TABLE 6

Mean evaporation of similar amounts (approximately 4 g) of formulation carriers from three replicate petri dishes, with a surface area of 60 cm³, in a fume hood at 26° C. at 1, 3, 7, and 24 hours:

| SOLVENT | TIME (hours) | APPROXIMATE MEAN PERCENT EVAPORATION (by weight) |
|---|---|---|
| ALIPHATIC | 1 | 5 |
| | 3 | 12 |
| | 7 | 30 |
| | 24 | 65 |
| AROMATIC | 1 | 1 |
| | 3 | 3 |
| | 7 | 6 |
| | 24 | 13 |
| KEROSENE | 1 | 13 |
| | 3 | 32 |
| | 7 | 52 |
| | 24 | 80 |
| MFAE | 1 | 0 |
| | 3 | 0 |
| | 7 | 0 |
| | 24 | 0 |

What is claimed is:

1. A nonaqueous herbicide formulation composition comprising, as the active ingredient, a herbicidally effective amount of triclopyr BEE, in admixture with one or more esters of vegetable oils as the carrier.

2. A composition of claim 1 wherein the carrier is selected from the group consisting of esters of corn oil, soybean oil, sunflower oil, canola oil, and cotton seed oil.

3. A composition of claim 2 wherein the carrier is selected from the group consisting of esters of soybean oil, sunflower oil, and canola oil.

4. A composition of claim 1 wherein the carrier is one or more fatty acid esters selected from the group consisting of $C_1$–$C_4$ straight or branched chain alkyl esters of $C_6$–$C_{18}$ saturated or unsaturated fatty acids.

5. A composition of claim 4 wherein the carrier is one or more methyl $C_6$–$C_{18}$ unsaturated fatty acid esters.

6. A composition of claim 5 wherein the carrier is one or more fatty acid esters selected from the group consisting of methyl caprylate-caprate, methyl laurate, and methyl oleate.

7. A composition of claim 6 wherein the fatty acid ester is methyl oleate.

8. A composition of claim 1, 2, 3, 4, 5, 6, or 7 comprising by % weight from about 4% to about 40% triclopyr BEE.

9. A composition of claim 1, 2, 3, 4, 5, 6, or 7 comprising by % weight from about 4% to about 20% triclopyr BEE.

10. A composition of claim 9 of the formula (by % weight):

| | |
|---|---|
| triclopyr BEE | 4.5% |
| methyl oleate | 95.5%. |

11. A composition of claim 9 of the formula (by % weight):

| | |
|---|---|
| triclopyr BEE | 13.6% |
| methyl oleate | 86.4%. |

12. A composition of claim 9 of the formula (by % weight):

| | |
|---|---|
| triclopyr BEE | 18.1% |
| methyl oleate | 81.9%. |

13. A nonaqueous herbicide formulation composition comprising, as the active ingredients, herbicidally effective amounts of triclopyr BEE and one or more other compatible herbicides, in admixture with one or more esters of vegetable oils as the carrier.

14. A composition of claim 13 comprising a herbicidally effective amount of triclopyr BEE and picloram EHE, in admixture with one or more esters of vegetable oils as the carrier.

15. A composition of claim 14 wherein the carrier is one or more fatty acid esters selected from the group consisting of methyl caprylate-caprate, methyl laurate, and methyl oleate.

16. A composition of claim 15 wherein the fatty acid ester is methyl oleate.

17. A composition of claim 16 of the formula (by % weight):

| | |
|---|---|
| triclopyr BEE | 11.7% |
| picloram EHE | 1.9% |
| methyl oleate | 86.4%. |

18. A method for controlling undesired vegetation which comprises basal or stem application of a herbicidal formulation composition of claim 1 to the vegetation desired to be treated.

19. A method of claim 18 wherein the carrier is selected from the group consisting of esters of corn oil, soybean oil, sunflower oil, and canola oil.

20. A method of claim 19 wherein the carrier is selected from the group consisting of esters of soybean oil, sunflower oil, and canola oil.

21. A method of claim 18 wherein the carrier is one or more fatty acid esters selected from the group consisting of $C_1$–$C_4$ straight or branched chain alkyl esters of $C_6$–$C_{18}$ saturated or unsaturated fatty acids.

22. A method of claim 21 wherein the carrier is one or more methyl $C_6$–$C_{18}$ unsaturated fatty acid esters.

23. A composition of claim 22 wherein the carrier is one or more fatty acid esters selected from the group consisting of methyl caprylate-caprate, methyl laurate, and methyl oleate.

24. A composition of claim 23 wherein the fatty acid ester is methyl oleate.

25. A method of claim 18, 19, 20, 21, 22, 23, or 24 wherein the composition comprises by % weight from about 4% to about 40% triclopyr BEE.

26. A method of claim 18, 19, 20, 21, 22, 23, or 24 wherein the composition comprises by % weight from about 4% to about 20% triclopyr BEE.

27. A method of claim 26 wherein the composition is of the formula (by % weight):

| | |
|---|---|
| triclopyr BEE | 4.5% |
| methyl oleate | 95.5%. |

28. A method of claim 26 wherein the composition is of the formula (by % weight):

| | |
|---|---|
| triclopyr BEE | 13.6% |
| methyl oleate | 86.4%. |

29. A method of claim 26 wherein the composition is of the formula (by % weight):

| | |
|---|---|
| triclopyr BEE | 18.1% |
| methyl oleate | 81.9%. |

30. A method for controlling undesired vegetation which comprises basal or stem application of a herbicidal formulation composition of claim 13 to the vegetation desired to be treated.

31. A method of claim 30 comprising a herbicidally effective amount of triclopyr BEE and picloram EHE, in admixture with one or more esters of vegetable oils as the carrier.

32. A method of claim 31 wherein the carrier is one or more fatty acid esters selected from the group consisting of methyl caprylate-caprate, methyl laurate, and methyl oleate.

33. A method of claim 32 wherein the fatty acid ester is methyl oleate.

34. A method of claim 33 wherein the composition is of the formula (by % weight):

| | |
|---|---|
| triclopyr BEE | 11.7% |
| picloram EHE | 1.9% |
| methyl oleate | 86.4%. |

* * * * *